(12) United States Patent
Jones et al.

(10) Patent No.: US 7,157,468 B2
(45) Date of Patent: Jan. 2, 2007

(54) PYRAZOLE DERIVATIVES

(75) Inventors: Lyn Howard Jones, Canterbury (GB); Charles Eric Mowbray, Eastry (GB); David Anthony Price, Deal (GB); Matthew Duncan Selby, Sandwich (GB); Paul Anthony Stupple, Canterbury (GB)

(73) Assignee: Pfizer Inc., San Diego, CA (US)

( * ) Notice: Subject to any disclaimer, the term of this patent is extended or adjusted under 35 U.S.C. 154(b) by 373 days.

(21) Appl. No.: 10/669,794

(22) Filed: Sep. 23, 2003

(65) Prior Publication Data

US 2005/0004129 A1   Jan. 6, 2005

Related U.S. Application Data

(60) Provisional application No. 60/433,220, filed on Dec. 13, 2002.

(30) Foreign Application Priority Data

Sep. 26, 2002  (GB) .................................. 0222375.8
Oct. 8, 2002   (GB) .................................. 0223357.5

(51) Int. Cl.
*A01N 43/42* (2006.01)
(52) U.S. Cl. .................. 514/310; 514/406; 544/350; 546/145; 548/364.7
(58) Field of Classification Search ............... 514/310; 546/145
See application file for complete search history.

(56) References Cited

U.S. PATENT DOCUMENTS

| | | | |
|---|---|---|---|
| 3,303,200 A | 2/1967 | Milton et al. | |
| 5,037,834 A | 8/1991 | Brighty et al. | |
| 6,933,312 B1 * | 8/2005 | Price et al. ................. | 514/406 |

FOREIGN PATENT DOCUMENTS

| | | |
|---|---|---|
| GB | 0223357.8 | 9/2002 |
| GB | 0223357.5 | 10/2002 |
| WO | WO 97/23462 | 7/1997 |
| WO | WO 98/30560 | 7/1998 |
| WO | WO 02/04424 | 1/2002 |
| WO | WO 02/30907 | 4/2002 |

OTHER PUBLICATIONS

U.S. Appl. No. 60/433,220, Pfizer Inc.
Berge, et. al., "Pharmaceutical Salts," *Journal of Pharmaceutical Sciences*, 1977, 1-19, vol. 66, No. 1.
Bighley, et. al., "Salt Forms of Drugs and Absorption," *Encyclopedia of Pharmaceutical Technology*, Marcel Dekker Inc., 1996, 453-497, vol. 13, New York.
Bungaard, et. al., *Design of Prodrugs*, 1985, Chapter 1, Elsevier Science Publishers, Amsterdam, New York, Oxford.
Carey, et. al., "Structure and Mechanisms," *Advanced Organic Chemistry*, 3rd Edition, Plenum Press, New York and London.
Ferres, et. al., "Pro-Drugs of β-Lactam Antibiotics," *Drugs of Today*, 1983, 499-538, vol. 19, No. 9.
Genin, et. al., "Novel 1,5-Diphenylpyrazole Nonnucleoside HIV-1 Reverse Transcriptase Inhibitors with Enhanced Activity Versus the Delavirdine-Resistant P236L Mutant: Lead Identification and SAR of 3- and 4-Substituted Derivatives," *Journal of Medicinal Chemistry*, 2000, 1034-1040, vol. 43, No. 5.
Greene, et. al., *Protective Groups in Organic Synthesis*, 1991, Second Edition, John Wiley & Sons, New York, Chichester, Brisbane, Toronto, Singapore.
Habermehl, et. al., "The Condensation of Histamine with Carbonyl Compounds," *Heterocycles*, 1976, 127, vol. 5, No. 1.
Katritzky, et. al., "The Structure, Reactions, Synthesis and Uses of Heterocyclic Compounds," *Comprehensive Heterocyclic Chemistry*, 1984, vol. 1-11, Pergamon Press, Oxford, New York, Toronto, Sydney, Paris, Frankfurt.
Topics in Chemistry, 306-316, (Not Available).

* cited by examiner

*Primary Examiner*—Kamal A. Saeed
(74) *Attorney, Agent, or Firm*—Keith D. Hutchinson; Bryan C. Zielinski

(57) ABSTRACT

This invention relates to pyrazole derivatives of formula (I)

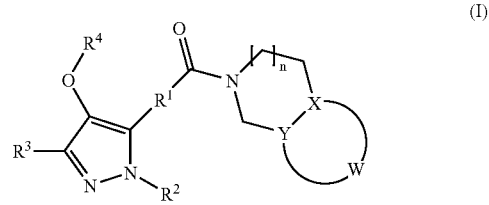

or pharmaceutically acceptable salts, solvates or derivative thereof, wherein $R^1$ to $R^4$, n W, X and Y are defined in the description, and to processes for the preparation thereof, intermediates used in their preparation of, compositions containing them and the uses of such derivatives.

The compounds of the present invention bind to the enzyme reverse transcriptase and are modulators, especially inhibitors thereof. As such the compounds of the present invention are useful in the treatment of a variety of disorders including those in which the inhibition of reverse transcriptase is implicated. Disorders of interest include those caused by Human Immunodificiency Virus (HIV) and genetically related retroviruses, such as Acquired Immune Deficiency Syndrome (AIDS).

3 Claims, No Drawings

PYRAZOLE DERIVATIVES

This application claims priority from United Kingdom application number 0222375.8, filed Sep. 26, 2002, United Kingdom application number 0223357.5, filed Oct. 8, 2002 and also claims the benefit of U.S. Provisional Application No. 60/433,220, filed Dec. 13, 2002, and incorporates each application by reference in its entirety.

BACKGROUND OF THE INVENTION

This invention relates to pyrazole derivatives, to their use in medicine, to compositions containing them, to processes for their preparation and to intermediates used in such processes.

Reverse transcriptase is implicated in the infectious lifecycle of Human Immunodeficiency Virus (HIV). Compounds which interfere with the function of this enzyme have shown utility in the treatment of conditions caused by HIV and genetically related retroviruses, such as Acquired Immune Deficiency Syndrome (AIDS). There is a constant need to provide new and better modulators, especially inhibitors, of HIV reverse transcriptase, since the virus is able to mutate, becoming resistant to the effects of known modulators.

Antiviral activity is ascribed to a class of N(hydroxyethyl) pyrazole derivatives in U.S. Pat. No. 3,303,200. A number of pyrazoles are disclosed as reverse transcriptase inhibitors, including: a class of N-phenylpyrazoles (*J. Med. Chem.*, 2000, 43, 1034); a class of C and S linked aryl pyrazoles (WO02/04424); and a class of O and S linked aryl pyrazoles, the O and S aryl link being adjacent to the nitrogen atom (WO02/30907).

SUMMARY OF THE INVENTION

According to the present invention there is provided a compound of formula (I)

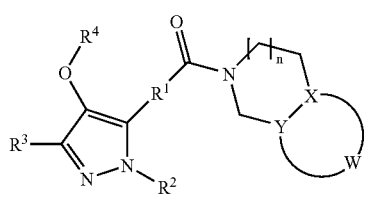

(I)

or a pharmaceutically acceptable salt, solvate or derivative thereof, wherein:

W—X—Y defines a five or six-membered partially saturated or aromatic ring containing 0 to 3 nitrogen atoms wherein X is CH or N and Y is CH or, when X is CH, may also be N; said ring being optionally substituted by halo, oxo, —CN, —$COR^5$, —$CONR^5R^5$, —$SO_2NR^5R^5$, —$NR^5SO_2R^5$, —$OR^5$, $OR^{11}$, —$NR^5R^5$, —($C_1$–$C_6$ alkylene)—$NR^5R^5$, $R^7$, $R^{11}$, or $CF_3$;

$R^1$ is $C_1$–$C_6$ alkylene;

$R^2$ is H, $C_1$–$C_6$ alkyl, $C_3$–$C_6$ alkenyl, $C_3$–$C_6$ alkynyl, $C_3$–$C_7$ cycloalkyl, $C_3$–$C_7$ cycloalkenyl, phenyl, benzyl, $R^8$ or $R^9$, said $C_1$–$C_6$ alkyl, $C_3$–$C_7$ cycloalkyl, phenyl and benzyl being optionally substituted by halo, —$OR^5$, —$OR^{10}$, —CN, —$CO_2R^7$, —$OCONR^5R^5$, —$CONR^5R^5$, —$C(=NR^5)NR^5OR^5$, —$CONR^5NR^5R^5$, —$NR^6R^6$, —$NR^5R^{10}$, —$NR^5COR^5$, —$NR^5COR^8$, —$NR^5COR_{10}$, —$NR^5CO_2R^5$, —$NR^5CONR^5R^5$, —$SO_2NR^5R^5$, —$NR^5SO_2R^5$, —$NR^5SO_2NR^5R^5$, $R^8$ or $R^9$;

$R^3$ is H, $C_1$–$C_6$ alkyl, $C_3$–$C_7$ cycloalkyl, phenyl, benzyl, halo, —CN, —$OR^7$, —$CO_2R^5$, —$CONR^5R^5$, $R^8$ or $R^9$, said $C_1$–$C_6$ alkyl, $C_3$–$C_7$ cycloalkyl, phenyl and benzyl being optionally substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$;

$R^4$ is phenyl, naphthyl or pyridyl, each being optionally substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{11}$, $So_xR^6$, O—($C_1$–$C_6$ alkylene)—$CONR^5R^5$, O—($C_1$–$C_6$ alkylene)—$NR^5R^5$, or O_($C_{1-}C_6$ alkylene)—$OR^6$;

each $R^5$ is independently either H, $C_1$–$C_6$ alkyl or $C_3$–$C_7$ cycloalkyl or, when two $R^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, fluoro($C_1$–$C_6$)alkyl or $C_3$–$C_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, —$C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN;

$R^{10}$ is $C_1$–$C_6$ alkyl substituted by $R^8$, $R^9$, —$OR^5$, —$CONR^5R^5$, —$NR^5COR^5$ or —$NR^5R^5$;

$R^{11}$ is phenyl optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, halo($C_1$–$C_6$)alkyl or $C_3$–$C_7$ cycloalkyl; and x and n are independently 0, 1 or 2.

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn-4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. Where $R^1$ and $R^2$ are taken together, they form, along with the nitrogen atom and the carbon atom of the pyrazole ring to which they are attached, a 5- or 6-membered ring. Where a heterocyclic group $R^8$ or $R^9$ is attached to an oxygen, sulphur or nitrogen heteroatom the heterocyclic group $R^8$ or $R^9$ must be linked through a ring carbon atom. Further, where a heterocyclic group $R^9$ is attached to an oxygen, sulphur or nitrogen heteroatom the heterocyclic group $R^9$ must be linked through a ring carbon atom that is not adjacent to a ring heteroatom.

The pharmaceutically acceptable salts of the compounds of formula (I) include the acid addition and the base salts thereof.

Suitable acid addition salts are formed from acids which form non-toxic salts and examples are the hydrochloride, hydrobromide, hydroiodide, chloride, bromide, iodide, sulphate, bisulphate, nitrate, phosphate, hydrogen phosphate, acetate, fumarate, pamoate, aspartate, besylate, carbonate, bicarbonate/, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts.

Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts.

For reviews on suitable salts see Berge et al, J. Pharm. Sci., 66, 1–19, 1977 and Bighley et al, Encyclopedia of Pharmaceutical Technology, Marcel Dekker Inc, New York, 1996, Vol 13, pp 453–497

The pharmaceutically acceptable solvates of the compounds of formula (I) include the hydrates thereof.

The compound of formula (I) may be modified to provide pharmaceutically acceptable derivatives thereof at any of the functional groups in the compound. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

The invention encompasses all isomers of the compound of formula (I) and pharmaceutically acceptable salts, solvates or derivatives thereof, including all geometric, tautomeric and optical forms, and mixtures thereof (e.g. racemic mixtures).

Separation of diastereoisomers may be achieved by conventional techniques, e.g. by fractional crystallisation, chromatography or high performance liquid chromatography (HPLC) of a stereoisomeric mixture of compounds. An individual enantiomer of a compound may also be prepared from a corresponding optically pure intermediate or by resolution, such as by HPLC of the corresponding racemate using a suitable chiral support, or by fractional crystallisation of the diastereoisomeric salts formed by reaction of the corresponding racemate with a suitable optically active acid or base, as appropriate.

The compound of formula (I) and pharmaceutically acceptable salts, solvates or derivatives thereof may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behaviour, and melting point of the compound are used to distinguish polymorphs.

Compounds of formula (I), pharmaceutically acceptable salts, solvates and derivatives thereof, isomers thereof, and polymorphs thereof, are hereinafter referred to as the compounds of the invention.

Preferred compounds of the invention are the compounds of formula (I) and pharmaceutically acceptable salts and solvates thereof.

Preferably, W-X—Y defines a five or six-membered partially saturated or aromatic ring containing 0 to 2 nitrogen atoms wherein X is CH or N and Y is CH or, when X is CH, may also be N; said ring being optionally substituted by halo, oxo, —CN, —$OR^5$, —$NR^5R^5$, —($C_1$–$C_6$ alkylene)—$NR^5R^5$, $R^7$, or $CF_3$.

Preferably, W-X—Y defines a five or six-membered partially saturated or aromatic ring containing 0 to 2 nitrogen atoms wherein X is CH or N and Y is CH or, when X is CH, may also be N; said ring being optionally substituted by oxo, —CN, —$C_1$–$C_6$ alkoxy, —$NH_2$, —N($C_1$–$C_6$ alkyl)($C_1$–$C_6$ alkyl), $C_1$–$C_6$ alkyl, or $CF_3$.

Preferably, W-X—Y defines a five or six-membered partially saturated or aromatic ring containing 0 to 2 nitrogen atoms wherein X is CH or N and Y is CH or, when X is CH, may also be N; said ring being optionally substituted by oxo, —CN, —$C_1$–$C_2$ alkoxy, —$NH_2$, —N($C_1$–$C_2$ alkyl)($C_1$–$C_2$ alkyl), $C_1$–$C_2$ alkyl, or $CF_3$.

Preferably, W-X—Y defines a six-membered aromatic ring containing 0 to 2 nitrogen atoms wherein X is CH or N and Y is CH or, when X is CH, may also be N, said ring being a phenyl, pyridinyl, pyrimidinyly or imidazolyl ring and said ring being optionally substituted by —CN, methoxy, —$NH_2$, methyl, or $CF_3$.

Preferably, $R^1$ is methylene or ethylene.

Preferably, $R^1$ is methylene.

Preferably, $R^2$ is H, $C_1$–$C_6$ alkyl, $C_3$–$C_6$ alkenyl, phenyl, benzyl or $R^9$, said phenyl, benzyl or $C_1$–$C_6$ alkyl being optionally substituted by halo, —$OR^5$, —$OR^{10}$, —CN, —$CO_2R^7$, —$OCONR^5R^5$, —$CONR^5R^5$, —C(=$NR^5$)$NR^5OR^5$, —$CONR^5NR^5R^5$, —$NR^6R^6$, —$NR^5R^{12}$, —$NR^5COR^5$, —$NR^5COR^8$, —$NR^5COR^{12}$, —$NR^5CO_2R^5$, —$NR^5CONR^5R^5$, —$SO_2NR^5R^5$, —$NR^5SO_2R^5$, $R^8$ or $R^9$.

Preferably, $R^2$ is H, $C_1$–$C_6$ alkyl, phenyl or benzyl, said $C_1$–$C_6$ alkyl being optionally substituted by halo, —$OR^5$, —$OR^{10}$ or —CN.

Preferably, $R^2$ is H, $C_1$–$C_3$ alkyl, phenyl or benzyl.

Preferably, $R^2$ is H.

Preferably, $R^3$ is H, $C_1$–$C_6$ alkyl or $C_3$–$C_7$ cycloalkyl, said $C_1$–$C_6$ alkyl being optionally substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$.

Preferably, $R^3$ is H or $C_1$–$C_6$ alkyl.

Preferably, $R^3$ is H or $C_1$–$C_4$ alkyl.

Preferably, $R^3$ is methyl or ethyl.

Preferably, R⁴ is phenyl optionally substituted by R⁸, halo, —CN, $C_1$–$C_6$ alkyl, $C_1$–$C_6$ haloalkyl, $C_3$–$C_7$ cycloalkyl or $C_1$–$C_6$ alkoxy.

Preferably, R⁴ is phenyl substituted by R⁸, halo, —CN, $C_1$–$C_6$ alkyl, or $C_1$–$C_6$ alkoxy.

Preferably, R⁴ is phenyl substituted by halo or —CN.

Preferably, R⁴ is phenyl substituted by chloro or —CN.

Preferably, R⁴ is 3,5-dicyanophenyl, 3,5-dichlorophenyl or 3-chloro-5-cyanophenyl.

Preferably, R⁸ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being optionally substituted by halo, —CN, —COR⁵, —CONR⁵R⁵, —SO₂NR⁵R⁵, —NR⁵SO₂R⁵, —OR⁵, —NR⁵R⁵, —($C_1$–$C_6$ alkylene)—NR⁵R⁵, $C_1$–$C_6$ alkyl, fluoro($C_1$–$C_6$)alkyl or $C_3$–$C_7$ cycloalkyl.

Preferably, R⁸ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by halo, —CN, —COR⁵, —CONR⁵R⁵, —SO₂NR⁵R⁵, —NR⁵SO₂R⁵, —OR⁵, —NR⁵R⁵, —($C_1$–$C_6$ alkylene)-NR⁵R⁵, $C_1$–$C_6$ alkyl, fluoro($C_1$–$C_6$)alkyl or $C_3$–$C_7$ cycloalkyl.

Preferably, R⁸ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —OR⁵, —NR⁵R⁵ or $C_1$–$C_6$ alkyl.

Preferably, R⁸ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —OH, —NH₂ or methyl.

Preferably, R⁹ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being optionally substituted by oxo, $C_1$–$C_6$ alkyl, $C_3$–$C_7$ cycloalkyl, —SO₂R⁵, —CONR⁵R⁵, —COOR⁵, —CO—($C_1$–$C_6$ alkylene)—OR⁵ or —COR⁵ and optionally substituted on a carbon atom which is not adjacent to a heteroatom by halo, —OR⁵, —NR⁵R⁵, —NR⁵COR⁵, —NR⁵COOR⁵, —NR⁵CONR⁵R⁵, —NR⁵SO₂R⁵ or —CN.

Preferably, R⁹ is azetidinyl, piperidinyl, tetrahydrofuranyl, piperazinyl or morpholinyl, each being optionally substituted by oxo, $C_1$–$C_6$ alkyl, $C_3$–$C_7$ cycloalkyl, —SO₂R⁵, —CONR⁵R⁵, —COOR⁵, —CO—($C_1$–$C_6$ alkylene)—OR⁵ or —COR⁵ and optionally substituted on a carbon atom which is not adjacent to a heteroatom by halo, —OR⁵, —NR⁵R⁵, —NR⁵COR⁵, —NR⁵COOR⁵, —NR⁵CONR⁵R⁵, —NR⁵SO₂R⁵ or —CN.

Preferably, R⁹ is azetidinyl, piperidinyl, tetrahydrofuranyl, piperazinyl or morpholinyl, each being optionally substituted by $C_1$–$C_6$ alkyl, —SO₂R⁵, —CONR⁵R⁵, —COOR⁵, —CO—($C_1$–$C_6$ alkylene)—OR⁵ or —COR⁵ and optionally substituted on a carbon atom which is not adjacent to a heteroatom by —OR⁵ or —NR⁵COR⁵.

Preferably, R⁹ is azetidinyl, piperidinyl, tetrahydrofuranyl, piperazinyl or morpholinyl, each being optionally substituted by —CH₃, —SO₂CH₃, —CONH₂, —COOCH₃, —COCH₂OCH₃ or —COCH₃ and optionally substituted on a carbon atom which is not adjacent to a heteroatom by —OCH₃ or —NHCOCH₃.

Preferably, R¹⁰ is $C_1$–$C_4$ alkyl substituted by R⁸, R⁹, —OR⁵, —CONR⁵R⁵, —NR⁵COR⁵ or —NR⁵R⁵.

Preferably, R¹⁰ is $C_1$–$C_4$ alkyl substituted by R⁹, —OR⁵, —NR⁵COR⁵ or —NR⁵R⁵.

Preferably, R¹⁰ is $C_1$–$C_2$ alkyl substituted by tetrahydrofuranyl, —OCH₃, —NHCOCH₃ or —NH₂.

Preferably, R¹¹ is phenyl substituted by halo, —CN, —COR⁵, —CONR⁵R⁵, —SO₂NR⁵R⁵, —NR⁵SO₂R⁵, —OR⁵, —NR⁵R⁵, —($C_1$–$C_6$ alkylene)-NR⁵R⁵, $C_1$–$C_6$ alkyl, halo($C_1$–$C_6$)alkyl or $C_3$–$C_7$ cycloalkyl.

Preferably, R¹¹ is phenyl substituted by halo, —CN, —CONR⁵R⁵, —SO₂NR⁵R⁵ or —OR⁵.

Preferably, R¹¹ is phenyl substituted by fluoro, —CN, —CONH₂, —SO₂NH₂ or —OCH³.

Preferably, n is 0 or 1.

Preferably, n is 1.

Preferred groups of compounds according to the invention include all combinations of the preferred definitions for individual substituents given above.

Preferred compounds of the invention are:

2-[4-(3,5-Dichloro-phenoxy)-5-methyl-2H-pyrazol-3-yl]-1-(3,4-dihydro-1H-isoquinolin-2-yl)-ethanone;

the compound of Example 17;

and pharmaceutically acceptable salts, solvates or derivatives thereof.

The compounds of the invention may have advantages over those of the prior art with regard to a number of useful properties or combinations thereof, such as potency, duration of action, pharmacokinetics, spectrum of activity, side effect profile, solubility, chemical stability, and so on.

The compounds of the invention may be prepared by any method known in the art for the preparation of compounds of analogous structure. The compounds of the invention can be prepared by the procedures described in the methods below, or by the specific methods described in the Examples, or by similar methods to either. The invention also encompasses any one or more of these processes for preparing the compounds of the invention, in addition to any novel intermediates used therein.

In the following methods, R¹, R², R³ and R⁴ are as previously defined for a compound of formula (I), unless otherwise stated; WSCDI is 1-(3-dimethylaminopropyl)-3-ethylcarbodiimide hydrochloride; AIBN is azobisisobutyronitrile; DCC is 1,3-dicyclohexylcarbodiimide; HBTU is O-benzotriazol-1-yl-N,N,N',N',-tetramethyluronium hexafluorophosphate; HOAT is 1-hydroxy-7-azabenzotriazol; HOBT is 1-hydroxybenzotriazole hydrate; PyBOP® is Benzotriazol-1-yloxytris(pyrrolidino)phosphonium hexafluorophosphate; PyBrOP® is bromo-tris-pyrrolidino-phosphonium hexafluorophosphate; Mukaiyama's reagent is 2-chloro-1-methylpyridinium iodide; KHMDS is potassium bis(trimethylsilyl)amide; LHMDS is lithium bis(trimethylsilyl)amide; NaHMDS is sodium bis(trimethylsilyl)amide; Hünig's base is N-ethyldiisopropylamine; Et₃N is triethylamine; NMM is N-methylmorpholine; DMA is N,N'-dimethylacetamide; MeOH is methanol, EtOH is ethanol; EtOAc is ethyl acetate; THF is tetrahydrofuran; DMSO is dimethyl sulphoxide; and DCM is dichloromethane.

Compounds of formula (I) may be prepared according to Scheme 1 that follows.

According to Scheme 1, compounds of formula (I) may be prepared by the reaction of an acid of formula (III) or an activated derivative thereof with an amine of formula (II) under conventional acid/amine coupling conditions.

Conveniently, the coupling is effected in the presence of an activating agent such as one of WSCDI or DCC, together with one of HOBT or HOAT; PYBOP®; PyBrOP®; HBTU; or Mukaiyama's reagent; optionally a base, such as a tertiary amine (e.g. NMM, Et₃N, or Hünig's base); a solvent, such as an ether (e.g. THF), a haloalkane (e.g. DCM) or a polar aprotic solvent (e.g. EtOAc or DMA); and at ambient to elevated temperature, such as ambient temperature.

Alternatively, the coupling is effected in the presence of an activating agent such as an acid halide (e.g. (COCl)$_2$); optionally a base, such as a tertiary amine (e.g. NMM, Et$_3$N, or Hünig's base); optionally a catalyst, such as 4-dimethylpyridine; a solvent, such as an ether (e.g. THF) or a haloalkane (e.g. DCM); and at ambient to elevated temperature, such as ambient temperature.

Acids of formula (III) may be prepared by hydrolysis of the corresponding nitrile of formula (IV) under conventional conditions. Conveniently the hydrolysis is effected in the presence of an acid, such as an inorganic acid (e.g. HCl); a solvent, such as an ether (e.g. dioxane); and at ambient to elevated temperature, such as elevated temperature (e.g. under reflux).

Compounds of formula (V) may be prepared by halogenation of a compound of formula (VI) using a source of halogen, such as a molecular halogen (e.g. bromine) or an N-halo-succinimide (e.g. N-bromo-succinimide), under conventional conditions. Conveniently the halogenation is effected in the presence of a solvent, such as a haloalkane (e.g. carbon tetrachloride or 1,1,1-trichloroethane); optionally a radical initiation catalyst, such as ultraviolet light or AIBN; and at ambient to elevated temperature, such as under reflux.

Compounds of formula (VI) may be prepared by the reaction of a compound of formula (VIII) with a hydrazine of formula (VII), or a salt or hydrate thereof. Conveniently, the reaction is effected a solvent, such as a protic solvent

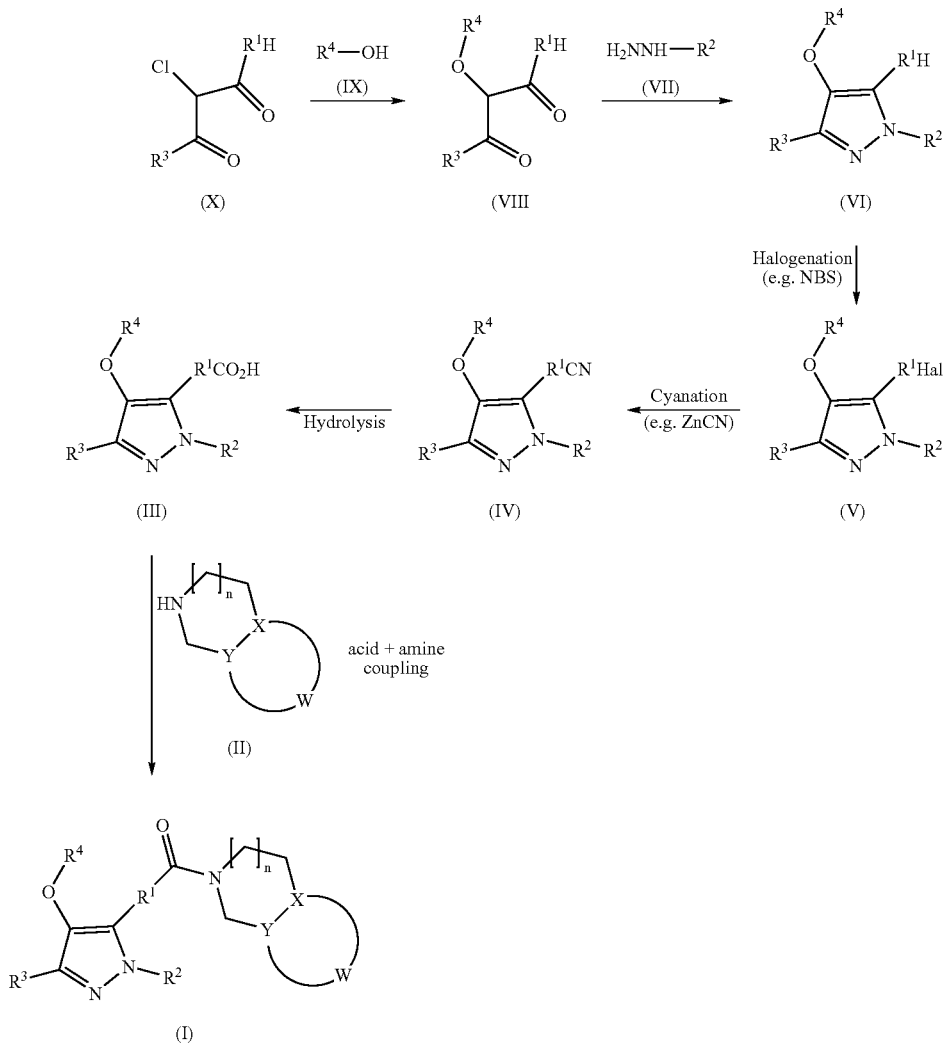

Scheme 1

Nitriles of formula (IV) may be prepared by cyanation of a compound of formula (V) using a source of cyanide, such as a metal cyanide (e.g. sodium, potassium, copper or zinc cyanide), under conventional conditions. Conveniently the cyanation is effected in the presence of a solvent, such as an ether (e.g. THF), a nitrile (e.g. acetonitrile) or water; and at ambient to elevated temperature, such as under reflux.

(e.g. acetic acid); at ambient to elevated temperature, such as ambient temperature; and optionally in the presence of an acid (e.g. acetic acid) or a base, such as a tertiary amine (e.g. triethylamine).

Compounds of formula (VIII) may be prepared by the reaction of a compound of formula (X) with an alcohol of formula (IX). Conveniently, the reaction is effected in the presence of a solvent, such as a polar solvent (e.g. acetone); a base, such as an inorganic base, preferably a metal carbonate (e.g. potassium or caesium carbonate); optionally, a nucleophilic catalyst, such as sodium iodide or tetrabutylammonium iodide; and at ambient to elevated temperature, such as elevated temperature (e.g. under reflux).

Chloroketoesters of formula (X) are either commercially available, known in the literature, or may be prepared by conventional methods (e.g. the chlorination of the corresponding ketoesters, for instance using sulphonyl chloride).

Compounds of formula (I) in which $R^3$ is halo can be prepared from a compound of formula (XI)

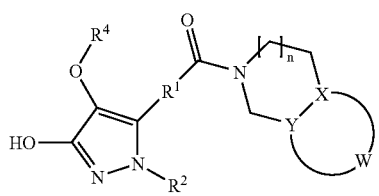

(XI)

under conventional conditions. Conveniently, the reaction is effected by an inorganic acid halide, such as an inorganic acid chloride (e.g. $POCl_3$); optionally in the presence of a solvent, such as a polar aprotic solvent (e.g. N,N-dimethylformamide); and at reduced to ambient temperature, such as ambient temperature.

Compounds of formula (XI) may be prepared using the routes described above, mutatis mutandis.

It will be appreciated by those skilled in the art that, in many cases, compounds of formula (I) may be converted into other compounds of formula (I) by functional group transformations, including for example the following interconversions.

Compounds of formula (I) in which $R^2$ is optionally substituted $C_1$–$C_6$ alkyl may be prepared from compounds of formula (I) in $R^2$ is H by reaction with an alkylating agent. Suitable alkylating agents include bromoacetonitrile, ethyl 4-chloroacetoacetate, methyl bromoacetate and chloroethylamine hydrochloride. Conveniently, alkylation is effected in the presence of a suitable solvent, such as an alcohol (e.g. ethanol) or a polar aprotic solvent (e.g. N,N-dimethylformamide); a base, such as a metal hydride (e.g. sodium hydride) or metal alkoxide (e.g. sodium ethoxide); and at ambient to elevated temperature, such as under reflux.

Compounds of formula (I) in which $R^2$ or $R^3$ contains a hydroxy group may be prepared from the corresponding compound of formula (I) in which $R^2$ or $R^3$ contains an ester group by reduction. Conveniently, the reduction is effected by a metal hydride agent, such as lithium aluminium hydride; in a solvent, such as an ether (e.g. diethyl ether); and at reduced temperature, such as from −78° C. to 0° C.

Compounds of formula (I) in which $R^2$ or $R^3$ are substituted by a heterocycle of formula $R^8$ and $R^9$ may be prepared by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11); and Compounds of formula (I) in which $R^3$ is —$CO_2H$ may be prepared by hydrolysis of a corresponding compound of formula (I) in which $R^3$ is —$CO_2R^5$. Conveniently, the reaction is effected in the presence of a solvent, such as an alcohol (e.g. aqueous ethanol), or an ether (e.g. aqueous 1,4-dioxan); and in the presence of a base, such as a metal hydroxide (e.g. sodium hydroxide). The skilled artisan will appreciate that such an acid may be converted into a primary amide by reaction with ammonia and a suitable coupling agent, such as a carbodiimide, e.g. dicyclohexylcarbodiimide, and that such a primary amide may then be converted into a nitrile by dehydration with a suitable dehydrating agent, such as phosphoryl chloride.

Compounds of formula (I) in which $R^3$ is $C_1$–$C_6$ alkyl may be converted into the compounds of formula (I) in which $R^3$ is $C_1$–$C_6$ alkyl substituted by halo (such as bromo), by halogenation, using a suitable halogenating agent. Conveniently the reaction is effected in the presence of a solvent, such as a haloalkane (e.g. dichloromethane) and at ambient temperature. Suitable halogenating agents include halogens (e.g. bromine) or N-halosuccinimides (e.g. N-bromsuccinimide).

Compounds of formula (I) containing an —OH, —NH— or —$NH_2$ group may be prepared by the deprotection of the corresponding compound bearing an —$OP^1$, —$NP^1$— or —$NHP^1$ group, respectively, wherein the group $P^1$ is a suitable protecting group. Examples of suitable protecting groups will be apparent to the skilled person; see, for instance, 'Protecting groups in Organic Synthesis (Second Edition)' by Theodora W. Green and Peter G. M. Wuts, 1991, John Wiley and Sons. Such compounds bearing an —$OP^1$, —$NP^1$— or —$NHP^1$ group may be prepared using the routes described above, mutatis mutandis.

Compounds of formulae (II), (VII) and (IX) are either commercially available, known in the literature or easily prepared by methods well known to those skilled in the art, such as those described in the Preparations hereinafter.

The compounds of the invention can be administered alone, but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the invention may also be administered as fast-dispersing or fast-dissolving dosage forms or in the form of a high energy dispersion or as coated particles. Suitable formulations of the compounds of the invention may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
|---|---|
| Compound of the invention | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention will usually be from 0.01 to 30 mg/kg, preferably from 0.01 to 5 mg/kg (in single or divided doses).

Thus tablets or capsules of the compound of the invention may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the invention may be taken as a single dose as needed or desired.

The compounds of invention can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO91/11172, WO94/02518 and WO98/55148.

It is to be appreciated that all references herein to treatment include curative, palliative and prophylactic treatment.

Oral administration is preferred.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immunocompromised state of the patient being treated.

Preferred combinations of the invention include simultaneous or sequential treatment with a compound of the invention and one or more:

(a) reverse transcriptase inhibitors such as abacavir, adefovir, didanosine, lamivudine, stavudine, zalcitabine and zidovudine;

(b) non-nucleoside reverse transcriptase inhibitors such as capavirine, delavirdine, efavirenz, and nevirapine;

(c) HIV protease inhibitors such as indinivir, nelfinavir, ritonavir, and saquinavir;

(d) CCR5 antagonists such as TAK-779 or UK-427, 857;

(e) CXCR4 antagonists such as AMD-3100;

(f) integrase inhibitors, such as L-870,810 or S-1360;

(g) inhibitors of viral fusion such as T-20;

(h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125;

(i) antifungal agents, such as fluconazole, itraconazole or voriconazole; or (j) antibacterial agents, such as azithromycin.

The activity of the compounds of the invention as reverse transcriptase inhibitors may be measured using the following assay.

Inhibition of HIV-1 Reverse Transcriptase Enzyme

Using purified recombinant HIV-1 reverse transcriptase (RT, EC, 2.7.7.49) obtained by expression in *Escherichia Coli*, a 96-well plate assay system is established for assaying a large number of samples using either the Poly(rA)-oligo (dT) Reverse Transcriptase [3H]-SPA enzyme assay system (Amersham NK9020) or the [3H]-flashplate enzyme assay system (NEN-SMP 103) and following the manufacturer's recommendations. The compounds are dissolved in 100% DMSO and diluted with the appropriate buffer to a 5% final DMSO concentration. The inhibitory activity is expressed in percent inhibition relative to DMSO control. The concentration at which compound inhibits reverse transcriptase by 50% is expressed as the $IC_{50}$ of the compound.

The compounds of Examples 8 and 17, when tested according to the above procedure, had $IC_{50}$ values of, respectively, 10 and 64 nanomolar.

Thus the invention provides:

(i) a compound of formula (I) or a pharmaceutically acceptable salt, solvate or derivative thereof;

(ii) a process for the preparation of a compound of formula (I) or a pharmaceutically acceptable salt, solvate or derivative thereof;

(iii) a pharmaceutical composition including a compound of formula (I) or a pharmaceutically acceptable salt, solvate or derivative thereof, together with a pharmaceutically acceptable excipient, diluent or carrier;

(iv) a compound of formula (I) or a pharmaceutically acceptable salt, solvate or composition thereof, for use as a medicament;

(v) a compound of formula (I) or a pharmaceutically acceptable salt, solvate or composition thereof, for use as a reverse transcriptase inhibitor or modulator;

(vi) a compound of formula (I) or a pharmaceutically acceptable salt, solvate or composition thereof, for use in the treatment of an HIV or genetically-related retroviral infection, or a resulting acquired immune deficiency syndrome (AIDS);

(vii) a use of the compound of formula (I) or of a pharmaceutically acceptable salt, solvate or composition thereof, for the manufacture of a medicament having reverse transcriptase inhibitory or modulating activity;

(viii) the use of a compound of formula (I) or of a pharmaceutically acceptable salt, solvate or composition thereof, for the manufacture of a medicament for the treatment of an HIV or genetically-related retroviral infection, or a resulting acquired immune deficiency syndrome (AIDS);

(ix) a method of treating an HIV or a genetically-related retroviral infection, or a resulting acquired immune deficiency syndrome (AIDS), comprising administering an effective amount of a compound of formula (I) or a pharmaceutically acceptable salt, solvate or composition thereof; and (xi) certain novel intermediates disclosed herein.

The following Examples illustrate the preparation of the compounds of formula (I). The synthesis of certain intermediates used therein are described in the Preparations section that follows the Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; $CDCl_3$, deuterochloroform; $D_6$-DMSO, deuterodimethylsulphoxide; $CD_3OD$, deuteromethanol. Where thin layer chromatography (TLC) has been used it refers to silica gel TLC using silica gel 60 $F_{254}$ plates, $R_f$ is the distance travelled by a compound divided by the distance travelled by the solvent front on a TLC plate.

Example 1

2-[4-(3,5-Dichloro-phenoxy)-5-methyl-2H-pyrazol-3-yl]-1-(7,8-dihydro-5H-[1,6]naphthyridin-6yl)-ethanone

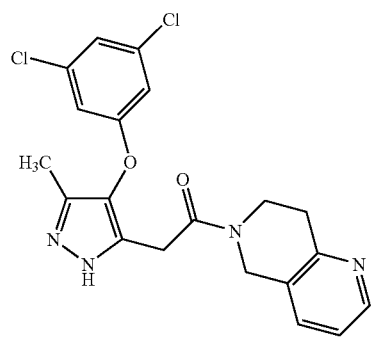

A solution of the acid from preparation 5 (50 mg, 0.17 mmol) in 3.75% triethylamine in N,N-dimethylacetamide (0.83 ml) was added to a solution of 5,6,7,8-tetrahydro-[1, 6]naphthyridine (38 mg, 0.25 mmol) (see U.S. Pat. No. 5,037,834, Example O) in 3.75% triethylamine in N,N-dimethylacetamide (1 ml) and a solution of O-benzotriazol- 1-yl-N,N,N',N',-tetramethyluronium hexafluorophosphate (94.75 mg, 0.25 mmol) in 3.75% triethylamine in N,N-dimethylacetamide (1 ml) was added. The mixture was heated at 50° C. under a nitrogen atmosphere for 4 hours and then was stirred at room temperature for 18 hours. The solvent was evaporated under reduced pressure and the residue was partitioned between 10% potassium carbonate solution (2 ml) and dichloromethane (6 ml). The organic layer was purified by chromatography on a Biotage™ cartridge using methanol in dichloromethane (gradient from 0:100 to 20:80) to give the title compound (53 mg).

$^1$H NMR (400 MHz, CDCl$_3$): δ 2.15 (s, 3H), 3.10 (m, 2H), 3.70 (m, 2H), 3.80 (m, 2H), 4.75 (s, 2H), 6.80 (s, 2H), 7.00 (s, 1H), 7.20 (m, 1H), 7.55 (m, 1H), 8.45 (s, 1H). LCMS: m/z ES$^-$ 415 [M−H]$^-$

Examples 2–7

The compounds of Table 1, of the general formula

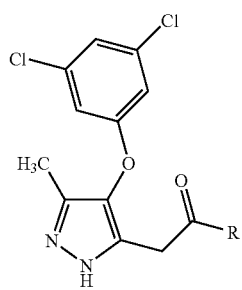

were prepared by a method analogous to that of Example 1, using the acid from preparation 5 and the appropriate amine.

TABLE 1

| Example No. | R group |
|---|---|
| 2 (see WO98/30560 Example 18d for the starting amine) | pyrido[3,4-d]pyrimidine tetrahydro group |
| 3 (see WO98/30560 Example 11c for the starting amine) | pyrido[4,3-d]pyrimidine tetrahydro group |
| 4 (see WO97/23462 Example 53c for the starting amine) | methoxy-pyrido[3,4-d]pyrimidine tetrahydro group |
| 5 (see Heterocycles 1976, 5(1), 127 for the starting amine) | tetrahydroimidazo[4,5-c]pyridine group |

TABLE 1-continued

| Example No. | R group |
|---|---|
| 6 (see Preparation 23 for the starting amine) | methoxy-tetrahydronaphthyridine group |
| 7 (see Synth. Commun. 1995, 25(20), 3255 for the starting amine) | cyano-tetrahydroisoquinoline group |

Example 2

$^1$H NMR (400 MHz, CD$_3$OD): δ 2.10 (s, 3H), 2.78 (m, 2H), 3.80 (m, 4H), 4.60 (s, 2H), 6.80, (m, 2H), 6.90 (s, 1H), 8.55 (s, 1H), 8.90 (s, 1H).

LCMS: m/z ES$^+$ 439 [M+H]$^+$

Accurate mass 418.0824, 420.0797

Example 3

$^1$H NMR (400 MHz, CD$_3$OD, rotamers): δ 2.10 (m, 3H), 2.85 (m, 2H), 3.77 (s, 2H), 3.85 (m, 2H), 4.68, 4.78 (2×s, 2H), 6.87 (m, 3H), 8.48, 8.54 (2×s, 1H), 8.91 (s, 1H).

LCMS: m/z ES$^+$ 418.2,419.2 [M+H]$^+$

Example 4

$^1$H NMR (400 MHz, CD$_3$OD, rotamers): δ 2.10 (m, 3H), 2.50 (m, 2H), 3.80 (m, 4H), 4.05, 4.07 (2×s, 3H), 4.55, 4.70 (2×s, 2H), 8.55, 8.60 (2×s, 1H).

LCMS: m/z ES$^+$ 448.2,450.1 [M+Na]$^+$

Example 5

$^1$H NMR (400 MHz, CD$_3$OD, rotamers): δ 2.10 (m, 3H), 2.65 (m, 2H), 3.76 (s, 2H), 4.82 (m, 2H), 4.54, 4.70 (2×s, 2H), 6.81 (m, 3H), 8.77 (s, 1H).

LCMS: m/z ES$^+$ 406.3,408.1 [M+H]$^+$

Example 6

$^1$H NMR (400 MHz, CD$_3$OD, rotamers): δ 2.05, 2.08 (2×s, 3H), 2.75 (m, 2H), 3.80 (m, 4H), 3.94 (s, 3H), 4.50, 4.65 (2×s, 2H), 6.89 (m, 4H), 7.52 (dd, 1H).

LCMS: m/z ES$^+$ 447,449 [M+Na]$^+$

Example 7

$^1$H NMR (400 MHz, CD$_3$OD, rotamers): δ 2.05, 2.08 (2×s, 3H), 2.80 (m, 2H), 4.75 (m, 4H), 4.60, 4.77 (2×s, 2H), 6.85 (m, 3H), 7.23 (dd, 1H), 7.52 (dd, 1H).

LCMS: m/z ES$^+$ 441,443 [M+Na]$^+$

Example 8

2-[4-(3,5-Dichloro-phenoxy)-5-methyl-2H-pyrazol-3-yl]-1-(3,4-dihydro-1H-isoquinolin-2-yl)-ethanone

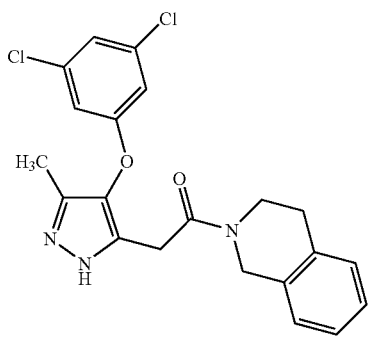

A mixture of the acid from preparation 5 (100 mg, 0.33 mmol), 1,2,3,4-tetrahydroisoquinoline hydrochloride (56 mg 0.33 mmol), 1-hydroxybenzotriazole hydrate (45 mg, 0.33 mmol), 1-(3-dimethylaminopropyl-3-ethylcarbodiimide hydrochloride (63 mg, 0.33 mmol) and triethylamine (92 µl, 0.66 mmol) in dichloromethane (5 ml) was stirred for 18 hours at room temperature. The reaction mixture was diluted with dichloromethane (5 ml) and was washed with water (5 ml), dried over magnesium sulphate and evaporated under reduced pressure. The residue was purified by chromatography on silica gel using methanol in ethyl acetate as eluant (0:100 to 10:90) to give the title compound as a yellow gum (62 mg).

$^1$H NMR (400 MHz, CDCl$_3$): δ 2.10 (d, 3H), 2.80 (m, 2H), 3.70 (m, 4H), 4.62 (d, 2H), 6.80 (m, 2H), 7.00 (m, 1H), 7.10 (m, 2H), 7.18 (m, 2H).

LRMS: M/Z APCI+ 416 [M+H]$^+$

Example 9

2-[4-(3,5-Dichloro-phenoxy)-5-methyl-2H-pyrazol-3-yl]-1-(1,3-dihydro-isoindol-2-yl)-ethanone

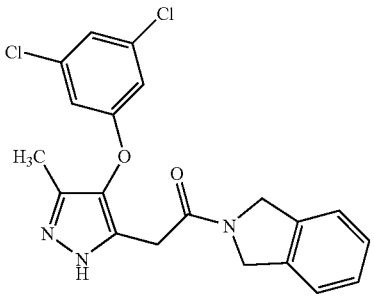

Triethylamine (59 µl, 0.43 mmol) was added to a solution of the acid from preparation 5 (120 mg, 0.38 mmol), 2,3-dihydro-1H-isoindole (51 mg 0.43 mmol), 1-hydroxybenzotriazole hydrate (57 mg, 0.43 mmol) and 1-(3-dimethylaminopropyl-3-ethylcarbodiimide hydrochloride (81 mg, 0.43 mmol) in dichloromethane (5 ml) and the mixture was stirred for 1 hour at room temperature. The reaction mixture was diluted with dichloromethane and was washed with 1N hydrochloric acid (5 ml). The dichloromethane solution was evaporated under reduced pressure and the residue was purified by chromatography on silica gel using methanol in dichloromethane (5:95) to give the title compound as a beige foam (90 mg).

$^1$H NMR (400 MHz, CDCl$_3$): δ 2.18 (s, 3H), 3.86 (s, 2H), 4.78 (m, 4H), 6.81 (s, 2H), 6.98 (s, 1H), 7.21 (m, 4H).

LRMS: m/z ES+ 424 [M+Na]$^+$

Example 10

3-Chloro-5-{3-methyl-5-[2-(2-methyl-7,8-dihydro-5H-pyrido[4,3-d]pyrimidin-6yl)-2-oxo-ethyl]-1H-pyrazol-4-yloxy}-benzonitrile

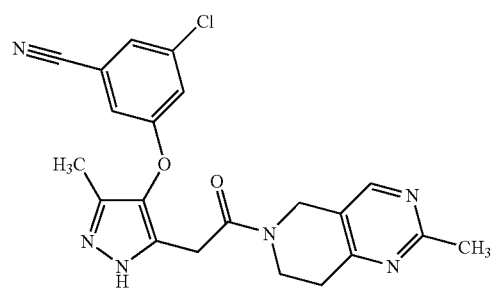

The carboxylic acid from preparation 13 (57 mg, 0.19 mmol) was added to 2-methyl-5,6,7,8-tetrahydro-pyrido[4,3-d]pyrimidine (29.4 mg, 1.9 mmol) (see WO98/30560 Example 17b), 1-hydroxybenzotriazole hydrate (26 mg, 0.19 mmol) and 1-(3-dimethylaminopropyl)-3-ethylcarbodiimide hydrochloride in dichloromethane (5 ml) containing triethylamine (79 µl, 0.57 mmol). The mixture was stirred at room temperature for 4 hours and then was diluted with dichloromethane (3 ml) and was washed with water (5 ml) dried over magnesium sulphate and evaporated under reduced pressure. The residue was purified by chromatography on a Biotage™ cartridge using methanol in dichloromethane as eluant (97.5:2.5 to 95:5) followed by further purification by chromatography on silica gel using methanol in dichloromethane (0:100 to 5:95) to give the title compound as a glass (33.2 mg).

$^1$H NMR (400 MHz, CDCl$_3$): δ 2.16 (d, 3H), 2.79 (m, 3H), 3.00 (m, 2H), 3.79 (m, 2H), 3.90 (m, 2H) 4.79 (d, 2H), 7.05 (m, 1H), 7.17 (m, 1H), 7.45 (m, 1H), 8.52 (d, 1H)

LRMS: M/Z APCI+ 423 [M+H]$^+$

Examples 11–19

The compounds of Table 2, of the general formula

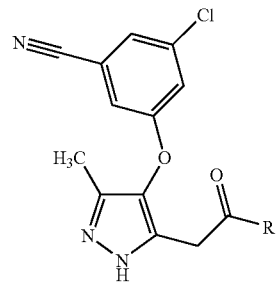

were prepared by a method analogous to that of Example 8, using the acid from preparation 13 and the appropriate amine.

TABLE 2

| Example Number | R group |
|---|---|
| 11 (see preparation 25 for the starting amine) | imidazo[1,2-a]pyrazine with CF3 |
| 12 (see US5,037,834 Example N for the starting amine) | tetrahydropyrido-pyrimidine-NH2 |
| 13 Isoindoline, Aldrich | isoindoline |
| 14 (see preparation 27 for the starting amine) | N-methyl tetrahydroisoquinolinone |
| 15 (see preparation 29 for the starting amine) | tetrahydronaphthyridinone |
| 16 (see WO98/30560 Example 18d for the starting amine) | tetrahydropyrido-pyrimidine |
| 17 1,2,3,4-tetrahydroisoquinoline, Aldrich | tetrahydroisoquinoline |
| 18 (see WO98/30560 Example 11c for the starting amine) | tetrahydropyrido-pyrimidine isomer |
| 19 (see US5,037,834 Example O for the starting amine) | tetrahydronaphthyridine |

Example 11

$^1$H NMR (400 MHz, CDCl$_3$): δ 2.16 (d, 3H), 3.78 (s, 1H), 4.04 (m, 4H), 4.80 (s, 2H), 7.10 (m, 1H), 7.18 (m, 1H), 7.20 (m, 1H), 7.25 (m, 1H).
MH+ 465

Example 12

$^1$H NMR (400 MHz, CDCl$_3$): δ 2.06 (m, 3H), 2.90 (m, 2H), 3.70 (s, 2H), 3.85 (m, 2H), 4.63 (s, 2H), 7.02 (m, 1H), 7.10 (m, 1H), 7.62 (m, 1H), 8.15 (d, 1H).
LRMS: M/Z APCI+ 424 [M+H]$^+$

Example 13

$^1$H NMR (400 MHz, CDCl$_3$): δ 2.2 (s, 3H), 3.72 (s, 2H), 4.78 (s, 2H), 4.82 (s, 2H), 7.10 (m, 1H), 7.18 (m, 1H), 7.25 (m, 5H).
LRMS: M/Z APCI+ 393 [M+H]$^+$

Example 14

$^1$H NMR (400 MHz, CDCl$_3$): δ 2.21 (d, 3H), 2.65 (m, 2H), 3.58 (m, 3H), 3.70 (m, 2H), 3.78 (m, 2H), 4.43 (d, 2H), 5.94 (m, 1H), 7.10 (m, 1H), 7.18 (m, 2H), 7.30 (m, 1H).
LRMS: M/Z APCI+ 438 [M+H]$^+$

Example 15

$^1$H NMR (400 MHz, CD$_3$OD): δ 2.10 (d, 3H), 2.58 (m, 2H), 3.75 (m, 4H), 4.30 (s, 1H), 4.55 (s, 1H), 6.40 (t, 1H), 7.24 (m, 4H),
LRMS: M/Z APCI+ 424 [M+H]$^+$

Example 16

$^1$H NMR (400 MHz, CDCl$_3$): δ 2.09 (d, 3H), 2.90 (m, 2H), 3.80 (m, 2H), 3.90 (t, 2H), 4.74 (d, 2H), 7.10 (m, 1H), 7.18 (m, 1H), 7.25 (m,1H), 8.55 (d, 1H), 9.00 (m, 1H).
LRMS: M/Z APCI+ 409 [M+H]$^+$

Example 17

$^1$H NMR (400 MHz, CD$_3$OD): δ 2.10 (d, 3H), 2.75 (m, 2H), 3.74 (m, 4H), 4.59 (m, 2H), 7.10 (m, 7H).
LRMS: M/Z APCI+ 407 [M+H]$^+$

Example 18

$^1$H NMR (400 MHz, CDCl$_3$): δ 2.13 (d, 3H), 3.02 (m, 2H), 3.90 (m, 4H), 4.76 (d, 2H), 7.05 (m, 1H), 7.18 (m, 1H), 7.25 (m, 1H), 8.56 (d, 1H), 9.01 (d, 1H).
LRMS: M/Z APCI+ 409 [M+H]$^+$

Example 19

$^1$H NMR (400 MHz, CDCl$_3$): δ 2.12 (d, 3H), 3.12 (m, 2H), 3.72 (m, 2H), 3.92 (m, 2H), 4.74 (m, 2H), 7.05 (m, 1H), 7.13 (m, 1H), 7.33 (m, 3H), 8.50 (m, 1H).
LCMS: m/z APCI+ 404 [M+H]$^+$

Example 20

5-{5-[2-(3,4-Dihydro-1H-isoquinolin-2-yl)-2-oxo-ethyl]-3-methyl-1H-pyrazol-4-yloxy}-isophthalonitrile

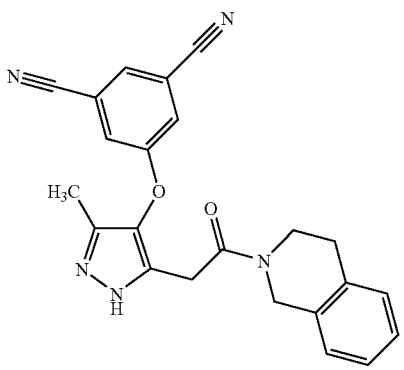

Triethylamine (42 μl, 0.3 mmol) was added to a suspension of the acid from preparation 21 (75 mg, 0.27 mmol), 1-hydroxybenzotriazole hydrate (40 mg, 0.3 mmol), 1-(3-dimethylaminopropyl-3-ethylcarbodiimide hydrochloride (58 mg, 0.3 mmol) and 1,2,3,4-tetrahydroisoquinoline hydrochloride (51 mg 0.3 mmol) in N,N-dimethylformamide (2.5 ml) and the mixture was stirred under a nitrogen atmosphere for 1 hour. The solvent was evaporated under reduced pressure with final traces of N,N-dimethylformamide being removed by toluene azeotrope. The residue was purified by chromatography on silica gel using methanol in dichloromethane (gradient from 2:98 to 5:95). The material isolated was further purified by chromatography on silica gel using pentane in ethyl acetate as eluant (25:75 then 20:80 then 0:100) to give the title compound (75 mg).

¹H NMR (400 MHz, CDCl₃): δ 2.20 (m, 3H), 2.80 (m, 2H), 3.70 (m, 2H), 3.80 (d, 2H), 4.60 (s, 2H), 7.25 (m, 7H).

LRMS: M/Z ES+ 398.2 [M+H]⁺

Preparation 1

4-(3,5-Dichlorophenoxy)-3,5-dimethyl-1H-pyrazole

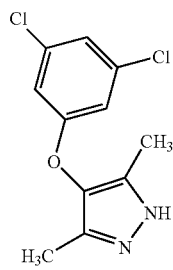

A mixture of 3-chloro-2,4-pentanedione (5.00 g, 37.0 mmol), 3,5-dichlorophenol (6.03 g, 37.0 mmol), caesium carbonate (12.0 g, 37.0 mmol) and acetone (40 ml) was heated at reflux for 18 hours. The mixture was cooled to room temperature, the solid was removed by filtration and the filtrate was evaporated under reduced pressure. The residue was dissolved in ethanol (30 ml) and hydrazine hydrate (1.85 g, 37.0 mmol) was added and the mixture was heated at 60° C. for 30 minutes. The mixture was concentrated under reduced pressure and the residue purified by chromatography on silica gel eluting with ethyl acetate in pentane (30:70) to give the title compound as a yellow solid (3.0 g).

m.p. 85–87° C.

¹H-NMR (300 MHz, CDCl₃): δ 2.14 (s, 6H), 5.24 (s, 1H), 6.81 (s, 2H), 7.02 (s, 1H).

LRMS: m/z TS+ 257 [M+H⁺].

Preparation 2

1-Acetyl-4-(3,5-dichlorophenoxy)-3,5-dimethyl-1H-pyrazole

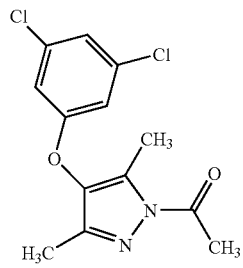

Sodium hydride (60% dispersion in mineral oil, 684 mg, 17.1 mmol) was added to a stirred solution of acetyl chloride (1.21 ml, 17.1 mmol) and the pyrazole of Preparation 1 (4.0 g, 15.6 mmol) in N,N-dimethylformamide (20 ml) at 0° C. under a nitrogen atmosphere. The reaction was stirred at 0° C. for 1 hour and then water (100 ml) was added. The aqueous solution was extracted with diethyl ether (2×50 ml). The combined organic phases were washed with water (30 ml) and brine (30 ml), dried over magnesium sulphate, filtered and evaporated under reduced pressure to leave a yellow solid. The crude product was purified by chromatography on silica gel using diethyl ether in pentane (10:90) as eluant to give the title compound as a white solid (3.0 g).

¹H-NMR (300 MHz, CDCl₃): δ 2.11 (s, 3H), 2.43 (s, 3H), 2.70 (s, 3H), 6.78 (s, 2H), 7.03 (s, 1H).

LRMS: m/z TS+ 299 [M+H⁺].

Preparation 3

1-Acetyl-3-(bromomethyl)-4-(3,5-dichlorophenoxy)-5-methyl-1H-pyrazole

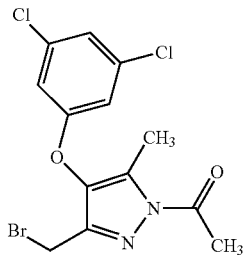

N-Bromosuccinimide (2.70 g, 15.0 mmol) was added to a stirred solution of the pyrazole of Preparation 2 (3.0 g, 10.0 mmol) in 1,1,1-trichloroethane (40 ml) at room temperature under a nitrogen atmosphere. The mixture was heated at 80° C. for 1 hour and then azobisisobutyronitrile (2 mg) was added and the mixture was heated for a further 3 hours. The reaction was cooled to room temperature and a solid formed was removed by filtration. The filtrate was evaporated under reduced pressure and the resulting yellow oil was dissolved in ethyl acetate (100 ml). The ethyl acetate solution was washed with 1M aqueous sodium carbonate solution (30 ml), water (30 ml) and brine (30 ml), dried over magnesium sulphate, filtered and evaporated under reduced pressure to leave a yellow solid. The crude product was purified by chromatography on silica gel using ethyl acetate in pentane (10:90) as eluant to give a yellow solid that was washed with ice cold diethyl ether (20 ml) to provide the title compound as a white solid (2.3 g).

m.p. 111–113° C.

$^1$H-NMR (300 MHz, CDCl$_3$): δ 2.10 (s, 3H), 2.73 (s, 3H), 4.73 (s, 2H), 6.86 (s, 2H), 7.11 (s, 1H).

LRMS: m/z TS+ 379 [M+H$^+$].

Preparation 4

[4-(3,5-Dichlorophenoxy)-3-methyl-1H-pyrazol-5-yl]acetonitrile

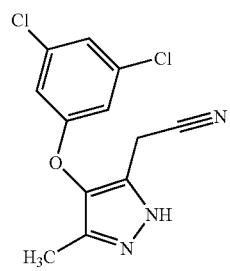

The bromomethyl pyrazole of Preparation 3 (1.00 g, 2.60 mmol) in tetrahydrofuran (10 ml) was added in one portion to a solution of sodium cyanide (284 mg, 5.20 mmol) in water (10 ml) at room temperature. The reaction was heated at 80° C. for 14 hours and cooled to room temperature. The solvent was evaporated under reduced pressure and the residue was partitioned between dichloromethane (50 ml) and water (50 ml). The organic layer was separated, washed with water (50 ml), brine (30 ml), dried over magnesium sulphate, filtered and the solvent evaporated under reduced pressure to give a brown solid. The residue was purified by chromatography on silica gel using pentane in ethyl acetate as eluant (50:50) to give the title compound as a yellow solid (500 mg).

m.p. 150–152° C.

$^1$H NMR (400 MHz, CDCl$_3$): δ 2.17 (s, 3H), 3.56 (s, 2H), 6.77 (s, 2H), 7.02 (s, 1H).

LRMS: m/z TS+ 282 [M+H]$^+$.

Preparation 5

[4-(3,5-Dichlorophenoxy)-3-methyl-1H-pyrazol-5-yl]acetic acid

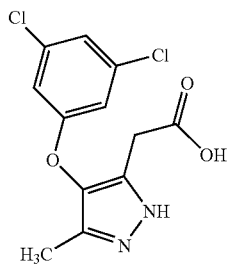

The nitrile of Preparation 4 (400 mg, 1.41 mmol) in concentrated hydrochloric acid (20 ml) was stirred at 100° C. for 14 hours. The mixture was cooled to room temperature and the solvent evaporated under reduced pressure. The residue was partitioned between dichloromethane (50 ml) and 1N aqueous hydrochloric acid (50 ml). The dichloromethane layer was washed with 1N aqueous hydrochloric acid (50 ml), dried over magnesium sulphate, filtered and the solvent evaporated under reduced pressure to give the title compound as pale yellow solid (400 mg).

m.p. 156–158° C.

$^1$H NMR (400 MHz, CD$_3$OD): δ 2.02 (s, 3H), 4.89 (s, 2H), 6.82 (s, 2H), 7.02 (s, 1H).

LRMS: m/z TS+ 303 [M+H]$^+$.

Preparation 6

1-Bromo-3-chloro-5-methoxybenzene

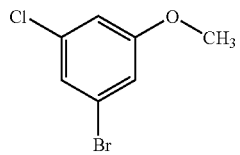

Sodium methoxide (4.5M solution in methanol, 2.20 ml, 10.0 mmol) was added dropwise to a stirred solution of 1-fluoro-3-chloro-5-bromobenzene (1.00 g, 4.77 mmol) in methanol (28 ml) at room temperature under a nitrogen atmosphere. The mixture was heated at reflux for 3 days and then cooled to room temperature. The mixture was evaporated under reduced pressure and the resulting yellow oil was dissolved in dichloromethane (30 ml). The dichloromethane solution was washed with water (2×20 ml) dried over magnesium sulphate, filtered and evaporated under reduced pressure. The residue was purified by chromatography on silica gel eluting with cyclohexane to provide the title compound as a colourless oil (302 mg).

$^1$H-NMR (400 MHz, CDCl$_3$): δ 3.77 (s, 3H), 6.82 (s, 1H), 6.94 (s, 1H), 7.09 (s, 1H).

Microanalysis: Found: C, 37.94; H, 2.75. C$_7$H$_6$BrClO requires; C, 37.96; H, 2.73%.

Preparation 7

3-Chloro-5-methoxybenzonitrile

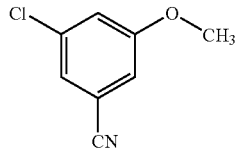

Palladium tetrakis(triphenylphosphine) (174 mg, 0.15 mmol) was added in one portion to a stirred solution of the bromide of Preparation 6 (500 mg, 2.26 mmol) and zinc cyanide (146 mg, 1.24 mmol) in N,N-dimethylformamide (3 ml) at room temperature under a nitrogen atmosphere. The reaction was heated at 100° C. for 14 hours and then cooled to room temperature. The solvent was evaporated under reduced pressure and the residue was purified by chromatography on silica gel using ethyl acetate in cyclohexane as eluant (5:95) to provide the title compound as a yellow oil (380 mg).

$^1$H-NMR (300 MHz, CDCl$_3$): δ 3.82 (s, 3H), 7.04 (s, 1H), 7.12 (s, 1H), 7.23 (s, 1H).

Microanalysis: Found: C, 57.50; H, 3.63; N, 8.16. C$_8$H$_6$ClNO requires; C, 57.33; H, 3.61; N, 8.36%.

Preparation 8

3-Chloro-5-hydroxybenzonitrile

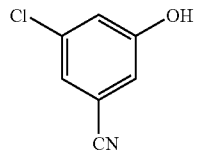

Boron trichloride (1.0M solution in dichloromethane, 26.0 ml, 26.0 mmol) was added dropwise to a stirred solution of the nitrite of Preparation 7 (1.80 g, 10.0 mmol) and tetrabutylammonium iodide (4.36 g, 11.0 mmol) in dichloromethane (50 ml) at −78° C. The reaction mixture was warmed to room temperature and stirred for 14 hours. The reaction mixture was cooled to 0° C. and ice and dichloromethane (100 ml) were added. The organic phase was washed with water (3×40 ml) and brine (40 ml), dried over magnesium sulphate, filtered and concentrated under reduced pressure. The residue was purified by chromatography on silica gel using ethyl acetate in cyclohexane as eluant (20:80) to give the title compound as a white solid (900 mg).

$^1$H-NMR (400 MHz, DMSO d$_6$): δ 7.12 (m, 2H), 7.38 (s, 1H), 10.65 (s, 1H).

Microanalysis: Found: C, 54.76; H, 2.81; N, 8.94. C$_7$H$_4$ClNO requires; C, 54.75; H, 2.63; N, 9.12%.

Preparation 9

3-(1-Acetyl-2-oxopropoxy)-5-chlorobenzonitrile

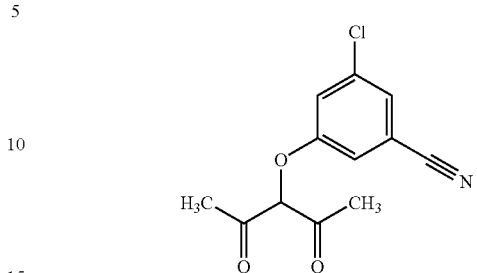

A mixture of 3-chloro-2,4-pentanedione (6.73 g, 50.0 mmol), the phenol of Preparation 8 (7.67 g, 50.0 mmol), caesium carbonate (18.0 g, 55.4 mmol) and acetone (40 ml) was heated at reflux for 2 hours. The reaction was cooled to room temperature, N,N-dimethylformamide (6 ml) and acetone (30 ml) were added and the reaction was heated at 70° C. for a further 12 hours. The mixture was cooled to room temperature and the solid was removed by filtration and dissolved in 1M aqueous hydrochloric acid (150 ml). The aqueous solution was extracted with dichloromethane (3×100 ml) and the combined organic phases were washed with brine (30 ml), dried over magnesium sulphate, filtered and concentrated under reduced pressure to provide the title compound as a brown solid (5.5 g).

m.p. 105–108° C.

$^1$H-NMR (300 MHz, CDCl$_3$): δ 2.04 (s, 6H), 7.13 (s, 1H), 7.19 (s, 1H), 7.35 (s, 1H), 14.40 (s, 1H).

Preparation 10

3-[(1-Acetyl-3,5-dimethyl-1H-pyrazol-4-yl)oxy]-5-chlorobenzonitrile

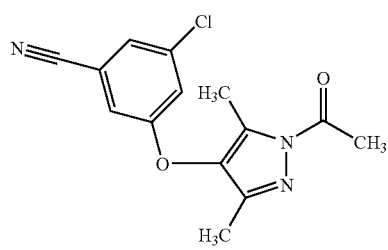

Sodium hydride (60% dispersion in oil, 840 mg, 21.0 mmol) was added to a stirred solution of acetyl chloride (1.50 ml, 21.0 mmol) and the pyrazole of Preparation 9 (4.80 g, 19.4 mmol) in N,N-dimethylformamide (20 ml) at 0° C. under a nitrogen atmosphere. The reaction was stirred at 0° C. for 15 minutes and then water (200 ml) was added. The aqueous mixture was extracted with ethyl acetate (3×120 ml). The combined organic phases were washed with water (50 ml) and brine (50 ml), dried over magnesium sulphate, filtered and evaporated under reduced pressure to leave a yellow solid. The crude product was purified by chromatography on silica gel using dichloromethane as eluant to give the title compound as a white solid (5.00 g).

$^1$H-NMR (400 MHz, CDCl$_3$): δ 2.06 (s, 3H), 2.38 (s, 3H), 2.65 (s, 3H), 6.99 (m, 1H), 7.08 (m, 1H), 7.29 (m, 1H).

LRMS: m/z TS+ 290 [M+H]$^+$.

Preparation 11

3-{[1-Acetyl-3-(bromomethyl)-5-methyl-1H-pyrazol-4-yl]oxy}-5-chlorobenzonitrile

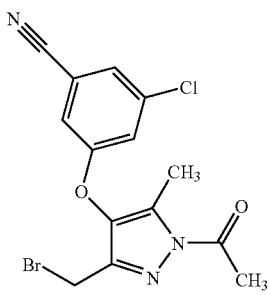

N-Bromosuccinimide (4.60 g, 25.6 mmol) was added to a stirred solution of the pyrazole of Preparation 10 (5.00 g, 17.3 mmol) in 1,1,1-trichloroethane (70 ml) and azobisisobutyronitrile (20 mg) at room temperature under a nitrogen atmosphere. The reaction was heated at 80° C. for 3 hours and then cooled to room temperature. A second portion of N-bromosuccinimide (2.0 g, 11.2 mmol) was added and the reaction mixture was heated at 80° C. for 4 hours. The reaction was cooled to room temperature and evaporated under reduced pressure and the resulting yellow oil was purified by chromatography on silica gel using pentane in dichloromethane as eluant (25:75) to give the title compound as a white solid (2.30 g).

m.p. 122–123° C.

$^{1}$H-NMR (400 MHz, CDCl$_{3}$): δ 2.10 (s, 3H), 2.74 (s, 3H), 4.73 (s, 2H), 7.12 (s, 1H), 7.22 (s, 1H), 7.39 (s, 1H).

Preparation 12

3-Chloro-5-(3-cyanomethyl-5-methyl-1H-pyrazol-4-yloxy)-benzonitrile

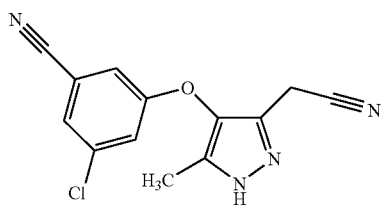

Sodium cyanide (450 mg, 9.2 mmol) in water (5 ml) was added dropwise to a stirred solution of the bromide from preparation 11 (1.7 g, 4.6 mmol) in tetrahydrofuran (30 ml) at 0° C. The mixture was warmed to room temperature and was stirred for 18 hours. The reaction mixture was concentrated under reduced pressure and the residue was diluted with ethyl acetate (30 ml) and washed with brine (2×15 ml), dried over magnesium sulphate, filtered and evaporated under reduced pressure. The residue was purified by chromatography on silica gel using ethyl acetate in pentane as eluant (0:100 to 50:50) to give the title compound as a pale orange solid (0.8 g).

m.p. 170–172° C.

$^{1}$H-NMR (400 MHz, CDCl$_{3}$): δ 2.10 (s, 3H), 3.60 (s, 2H), 7.05 (m, 1H), 7.15 (m, 1H), 7.33 (m, 1H).

Preparation 13

[4-(3-Chloro-5-cyano-5-phenoxy)-5-methyl-1H-pyrazol-3-yl]-acetic acid

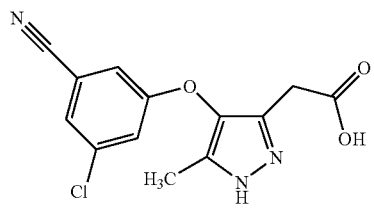

The cyanomethyl compound from preparation 12 (340 mg, 1.25 mmol) in 4N hydrochloric acid was heated at 80° C. for 18 hours. The mixture was evaporated under reduced pressure. The residue was dissolved in dichloromethane and silica gel was added. The solvent was evaporated under reduced pressure and the residue was purified by chromatography on silica gel using methanol in dichloromethane as eluant (0:100 to 20:80) to give the title compound (50 mg).

m.p. 175–178° C.

$^{1}$H NMR (400 MHz, CD$_{3}$OD): δ 2.10 (s, 3H), 3.52 (s, 2H), 7.20 (m, 1H), 7.25 (m, 1H) 7.43 (m, 1H).

Preparation 14

1,3-Dibromo-5-methoxybenzene

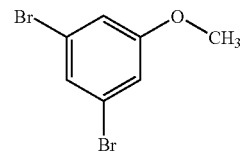

Sodium methoxide (4.5M solution in methanol, 8.80 ml, 41.0 mmol) was added dropwise to a stirred solution of 3,5-dibromofluorobenzene (5.00 g, 19.0 mmol) in N,N-dimethylformamide (95 ml) at 0° C. under a nitrogen atmosphere. The reaction was warmed to room temperature, stirred for 1 hour and then evaporated under reduced pressure. The residue was dissolved in diethyl ether and was washed with water (3×300 ml) and brine (300 ml), dried over magnesium sulphate, filtered and concentrated under reduced pressure to give the title compound as a white solid (5.13 g).

$^{1}$H-NMR (300 MHz, CDCl$_{3}$): δ 3.79 (s, 3H), 7.00 (s, 2H), 7.26 (s, 1H).

LRMS: m/z TS+ 266 [M+H]$^{+}$.

Preparation 15

3,5-Dicyanomethoxybenzene

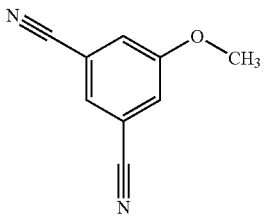

Tris(dibenzylideneacetone)dipalladium(0) (6.53 g, 7.15 mmol) was added in one portion to a stirred solution of the bromide of Preparation 1 (38.0 g, 143 mmol), 1,1'-bis(diphenylphosphino)ferrocene (9.3 g, 16.8 mmol) and zinc cyanide (20.0 g, 172 mmol) in N,N-dimethylformamide (300 ml) at room temperature under nitrogen. The reaction was heated at 100° C. for 14 hours and cooled to room temperature. Water (1500 ml) was added and the mixture was extracted with ethyl acetate (3×500 ml). The combined organics were filtered and the filtrate was washed with water (500 ml), dried over magnesium sulphate, filtered and concentrated under reduced pressure. The resulting solid was triturated with toluene (1000 ml) to provide the title compound (18.0 g) as a tan solid.

$^1$H-NMR (300 MHz, CDCl$_3$): δ=3.83 (3H, s), 7.31 (2H, s), 7.48 (1H, s).

Preparation 16

3,5-Dicyanohydroxybenzene

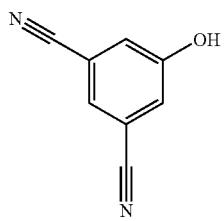

The ether of Preparation 15 (9.60 g, 60.7 mmol) was added portionwise to a stirred suspension of aluminium trichloride (32.4 g, 243 mmol) in dichloromethane (250 ml) at 0° C. under a nitrogen atmosphere. The suspension was stirred at 45° C. for 6 days, then cooled to room temperature and poured onto ice (450 ml). Concentrated hydrochloric acid (450 ml) was added dropwise and the resulting suspension was stirred for 10 minutes at room temperature. The solid formed was isolated by filtration, washed with water and dried over phosphorus pentoxide to give the title compound as a tan solid (7.83 g) [containing approximately 11% starting material by $^1$H-NMR and microanalysis].

$^1$H-NMR (400 MHz, CDCl$_3$): δ 7.36 (m, 2H), 7.56 (m, 1H).

Preparation 17

5-(3,5-Dimethyl-1H-pyrazol-4-yloxy)-isophthalonitrile

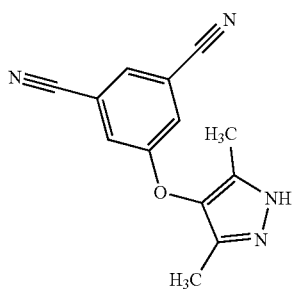

The phenol from preparation 16 (2 g, 13.8 mmol) was mixed with 3-chloro-2,4-pentanedione (2 ml, 16.7 mmol) and caesium carbonate (4.51 g, 13.8 mmol) and was heated at 65° C. for 2 hours. The mixture was cooled to room temperature and concentrated hydrochloric acid (2 ml) was added. The mixture was diluted with water (50 ml) and extracted with ethyl acetate (3×50 ml). The combined organic solutions were washed with brine, dried over magnesium sulphate and evaporated under reduced pressure. The residual yellow oil was dissolved in acetic acid (30 ml) and hydrazine (1 ml, 20.7 mmol) was added. The mixture was stirred at room temperature for 10 minutes and then evaporated under reduced pressure. The residue was dissolved in ethyl acetate (50 ml) and washed with 10% sodium carbonate solution (30 ml), water (30 ml) brine (30 ml) and then dried over magnesium sulphate. The solvent was evaporated under reduced pressure and the residue was triturated with diethyl ether to give the title compound as a pale yellow solid (1.8 g).

m.p. 182–185° C.

$^1$H-NMR (300 MHz, CDCl$_3$): δ 2.16 (s, 6H), 7.40 (s, 2H), 7.59 (s, 1H).

LRMS: m/z TS+ 239 [M+H]$^+$.

Preparation 18

5-[1-(2,2-Dimethyl-propionyl)-3,5-dimethyl-1H-pyrazol-4-yloxy]-isophthalonitrile

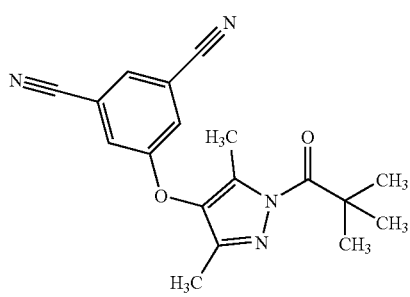

The pyrazole from preparation 17 (10 g, 41.7 mmol) was dissolved in N,N-dimethylformamide (60 ml) and was cooled to 0° C. 2,2-Dimethyl propionyl chloride (7.6 ml, 62.6 mmol) and then sodium hydride (60% in mineral oil, 2.5 g, 62.5 mmol) was added. The mixture was stirred at 0° C. for 30 minutes and then a saturated solution of ammonium chloride (50 ml) was added. The reaction mixture was partitioned between water (200 ml) and ethyl acetate (200 ml). The aqueous phase was washed with ethyl acetate (200 ml) and the combined organic layers were washed with water (200 ml), brine (200 ml) dried over magnesium sulphate and evaporated under reduced pressure. The residue was purified by chromatography on silica gel using dichloromethane as eluant to give the title compound as a white solid (14 g).

$^{1}$H-NMR (400 MHz, CDCl$_{3}$): δ 1.56 (s, 9H), 2.09 (s, 3H), 2.39 (s, 3H), 7.39 (s, 2H), 7.61 (s, 1H).

Preparation 19

5-[5-Bromomethyl-1-(2,2-dimethyl-propionyl)-3-methyl-1H-pyrazol-4-yloxy]-isophthalonitrile

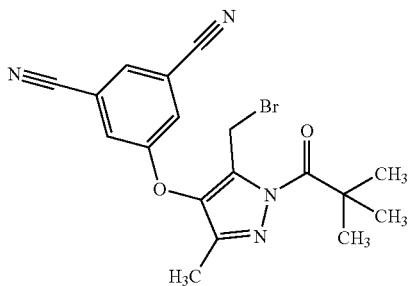

A solution of the pyrazole of preparation 18 (5 g, 15.5 mmol) and N-bromo succinimide (3 g, 17.08 mmol) in carbon tetrachloride (100 ml) was purged with nitrogen for 20 minutes. 2,2'-Azobis(2-methylpropionitrile) (123 mg, 0.78 mol) was added and the mixture was heated at 85° C. for 3 hours. The solvent was evaporated under reduced pressure and the residue was purified by chromatography on silica gel using dichloromethane in pentane (50:50) as eluant to give the title compound as a brown solid (5.7 g).

$^{1}$H-NMR (400 MHz, CDCl$_{3}$): δ 1.54 (d, 9H), 2.08 (s, 3H), 4.68 (s, 2H), 7.44 (s, 2H), 7.68 (s, 1H).

Preparation 20

5-(5-Cyanomethyl-3-methyl-1H-pyrazol-4-yloxy)-isophthalonitrile

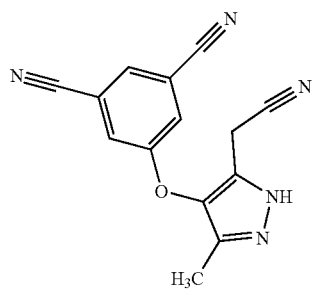

The bromide from preparation 19 (1.5 g, 3.7 mmol) in tetrahydrofuran (45 ml) was added to a solution of sodium cyanide (400 mg, 8.2 mmol) in water (7 ml) land the mixture was stirred at room temperature for 18 hours. The reaction mixture was concentrated under reduced pressure (to approximately 20 ml) and the residue was extracted with ethyl acetate (3×50 ml). The combined ethyl acetate layers were washed with brine (50 ml) dried over magnesium sulphate, filtered and evaporated under reduced pressure. The residue was purified by chromatography on silica gel using ethyl acetate in pentane as eluant (50:50 to 40:60) to give the title compound as a white solid (500 mg).

$^{1}$H NMR (400 MHz, DMSO-d$_{6}$): δ 2.05 (s, 3H), 3.82 (s, 2H), 7.72 (m, 2H), 8.12 (m, 1H).

LRMS: m/z ES+ 286 [M+Na]$^{+}$.

Preparation 21

[4-(3,5-Dicyano-phenoxy)-5-methyl-2H-pyrazol-3-yl]-acetic acid

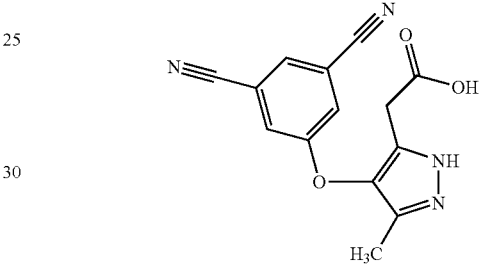

6N Hydrochloric acid (6 ml) was added to a suspension of the nitrile from preparation 20 in 1,4-dioxane (6 ml). The mixture was heated at 80° C. for 4 hours, then stirred at room temperature for 18 hours and then heated at 80° C. for 3 hours. The reaction mixture was evaporated under reduced pressure and the residue was purified by chromatography on silica gel using methanol in dichloromethane as eluant (gradient from 5:95 to 10:90) to give the title compound as a yellow solid (75 mg).

$^{1}$H NMR (400 MHz, DMSO-d$_{6}$): δ 2.00 (s, 3H), 3.41 (s, 2H), 7.68 (m, 2H), 8.08 (m, 1H).

LRMS: m/z APCI 283[M+H]$^{+}$.

Preparation 22

6-Benzyl-2-methoxy-5,6,7,8-tetrahydro-[1,6]naphthyridine

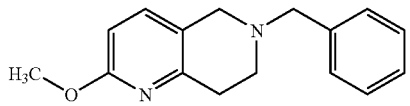

Sodium (2.49 g, 0.11 mol) was added portionwise to methanol (70 ml) and was stirred at room temperature under a nitrogen atmosphere for 30 minutes. N,N-dimethylformamide (35 ml) was added and the solution was added to 6-benzyl-2-chloro-5,6,7,8-tetrahydro-[1,6]naphthyridine (2.8 g, 10.9 mmol) (see reference WO98/30560 Example 33b). The mixture was heated at reflux under a nitrogen atmosphere for 5 days and then was evaporated under reduced pressure. The residue was purified by chromatography on silica gel using methanol in dichloromethane (gradient from 0:100 to 4:96) and the material obtained was dried under vacuum to give the title compound (2.54 g).

$^1$H-NMR (300 MHz, CDCl$_3$): δ 2.83 (t, 2H), 2.92 (t, 2H), 3.69 (s, 2H), 3.90 (s, 3H), 6.51 (d, 1H), 7.18 (d, 1H), 7.33 (m, 5H).

LCMS: m/z TS+ 255[M+H]$^+$

Preparation 23

2-Methoxy-5,6,7,8-tetrahydro-[1,6]naphthyridine

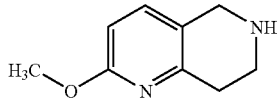

The N-benzyl compound of preparation 22 (2.33 g, 9.16 mmol) was mixed with 20% palladium on carbon (800 mg) in methanol (60 ml) and triethyl amine (2 ml). The mixture was hydrogenated at 50 psi for 2 days and then was filtered through Arbocel®. The filtrate was evaporated under reduced pressure and the residue was purified by chromatography on silica gel using methanol in dichloromethane containing ammonium hydroxide solution as eluant (gradientfrom 0:100:0 to 10:90:1). The material obtainedwas dried undervacuum to give the title compound (1.14 g).

$^1$H-NMR (300 MHz, CDCl$_3$): δ 2.82 (t, 2H), 3.20 (t, 2H), 3.89 (s, 3H), 3.95 (s, 2H), 6.54 (d, 1H), 7.21 (d, 1H).

LCMS: m/z TS+ 165 [M+H]$^+$

Preparation 24

2-Trifluoromethyl-imidazo[1,2-a]pyrazine

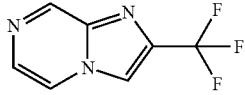

2-Aminopyrazine (12.5 g, 0.13 mol) and 3-bromo-1,1,1-trifluoro-propan-2-one (27.6 g, 0.14 mol) in ethanol (150 ml) was heated at reflux for 24 hours. A further portion of 3-bromo-1,1,1-trifluoro-propan-2-one (2.51 g, 14 mmol) was added and the mixture was heated at reflux for 18 hours. The solvent was evaporated under reduced pressure and the residue was dissolved in water (30 ml). Solid sodium hydrogen carbonate was added to bring the pH to 8 and the solution was extracted with dichloromethane (×3). The combined organic layers were washed with water (20 ml) dried over magnesium sulphate and evaporated under reduced pressure. The residue was purified by medium pressure chromatography on silica gel using methanol in dichloromethane as eluant (gradient from 2:98 to 4:96). The material isolated was further purified by chromatography on silica gel using methanol in dichloromethane as eluant (2:98). The material isolated was recrystallised from ethyl acetate/hexane to give the title compound as an orange brown solid (3 g).

Found; C, 44.81; H, 2.04; N, 22.15; C$_7$H$_4$F$_3$N$_3$ requires; C, 44.93; H, 2.15; N, 22.46%.

LRMS: m/z TS+ 188 [M+H]$^+$

Preparation 25

2-Trifluoromethyl-5,6,7,8-tetrahydro-imidazor[1,2-a]pyrazine hydrochloride

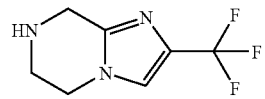

The compound from preparation 24 (4.15 g, 22.2 mmol), glacial acetic acid (5.72 ml, 0.11 mol) and rhodium 5% on alumina (900 mg) in anhydrous ethanol (80 ml) was hydrogenated at 50 psi and 50° C. for 6 hours. The reaction mixture was filtered and the filtrate was evaporated under reduced pressure. The residue was dissolved in ethanol (50 ml) and 1N hydrochloric acid (50 ml) was added. The solvent was evaporated under reduced pressure and the residue was dried by toluene azeotrope. The resulting material was recrystallised from ethanol/hexane to give the title compound (4.26 g).

MH+ 192.

Preparation 26

2-Methyl-2H-[2,6]naphthyridin-1-one

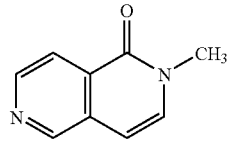

Sodium hydride (60% in mineral oil, 328 mg, 8.2 mmol) was added portionwise to a suspension of 2H-[2,6]naphthyridin-1-one (1 g, 2.05 mmol) (see reference J. Het. Chem. 1981, 18(7), 1349) in anhydrous N,N-dimethylformamide (25 ml) under a nitrogen atmosphere and the mixture was stirred at room temperature for 1 hour. Iodomethane (510 µl, 8.2 mmol) was added and the mixture was stirred for 18 hours. The reaction mixture was evaporated under reduced pressure and the residue was partitioned between dichloromethane (50 ml) and water (20 ml). The aqueous phase was extracted with dichloromethane (2×30 ml) and the combined organic layers were dried over magnesium sulphate and evaporated under reduced pressure. The residue was purified by chromatography on silica gel using methanol in dichloromethane (gradient from 2:98 to 5:95) to give the title compound (750 mg).

$^1$H-NMR (300 MHz, CDCl$_3$): δ 3.62 (s, 3H), 6.58 (d, 1H), 7.20 (d, 1H), 8.19 (d, 1H), 8.68 (d, 1H), 8.99 (s, 1H). LCMS: m/z TS+ 161[M+H]$^+$.

Preparation 27

2-Methyl-5,6,7,8-tetrahydro-2H-[2,6]naphthyridin-1-one

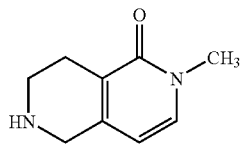

The compound from preparation 26 (87 mg, 0.54 mmol) was dissolved in anhydrous ethanol (30 ml) and platinum oxide (50 mg) was added and the mixture was hydrogenated at 50 psi for 18 hours. The reaction mixture was filtered and the filtrate was evaporated under reduced pressure to give the title compound as a brown gum (39 mg).

LCMS: m/z TS+ 165 [M+H]$^+$.

Preparation 28

6-Benzyl-5,6,7,8-tetrahydro-1H-[1,6]naphthyridin-2-one

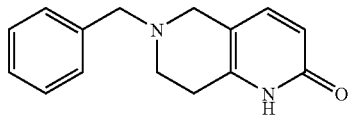

Bromine (750 μl, 14.6 mmol) in glacial acetic acid (5 ml) was added dropwise over 5 minutes to (6-benzyl-3,4,5,6,7,8-hexahydro-1H-[1,6]naphthyridin-2-one (3.37 g, 13.9 mmol) (reference WO9830560) dissolved in glacial acetic acid (50 ml) at 100° C. The mixture was heated at 100° C. for 2.5 hours and then was cooled to room temperature. The solvent was evaporated under reduced pressure and the residue was basified with 10% sodium carbonate solution (50 ml). The aqueous mixture was extracted with chloroform (4×50 ml) and the combined organic solutions were dried over sodium sulphate and evaporated under reduced pressure. The residue was purified by chromatography on silica gel using methanol in dichloromethane (gradient from 0:100 to 3:97) to give the title compound as yellow crystals (1.5 g).

M.p. 210–212° C.

Found C, 75.04; H, 6.74; N, 11.88; $C_{15}H_{16}N_2O$ requires; C, 74.97; H, 6.71; N; 11.66%

Preparation 29

5,6,7,8-tetrahydro-1H-[1,6]naphthyridin-2-one

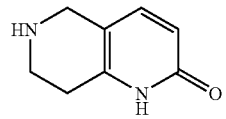

A mixture of the N-benzyl compound from preparation 28 (1.11 g, 4.63 mmol) and 10% palladium on activated carbon (150 mg) in glacial acetic acid was hydrogenated at 60 psi and room temperature for 18 hours. The mixture was filtered and the solvent was evaporated under reduced pressure. The residue was re-dissolved in glacial acetic acid and a further portion of 10% palladium on activated carbon (150 mg) was added. The mixture was hydrogenated at 60 psi for 20 hours and then was filtered. The filtrate was evaporated under reduced pressure and the residue was triturated with diethyl ether (2×40 ml). The solid obtained was recrystallised from methanol/ethyl acetate to give the title compound as buff crystals (550 mg).

M.p. 243–246° C.

The invention claimed is:

1. A compound of formula (I)

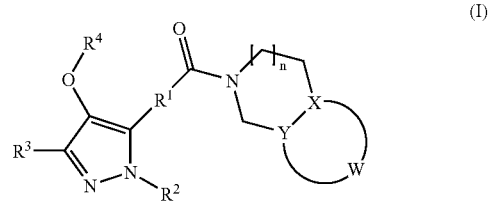

or a pharmaceutically acceptable salt, solvate or derivative thereof, wherein:

W-X—Y defines a five or six-membered partially saturated or aromatic ring containing 0 to 3 nitrogen atoms wherein X is CH or N and Y is CH or, when X is CH, Y, may also be N; said ring being optionally substituted by halo, oxo, —CN, —COR$^5$, —CONR$^5$R$^5$, —SO$_2$NR$^5$R$^5$, —NR$^5$SO$_2$R$^5$, —OR$^5$, OR$^{11}$, —NR$^5$R$^5$, —(C$_1$–C$_6$ alkylene)—NR$^5$R$^5$, R$^7$, R$^{11}$, or CF$_3$;

R$^1$ is C$_1$–C$_6$ alkylene;

R$^2$ is H, C$_1$–C$_6$ alkyl, C$_3$–C$_6$ alkenyl, C$_3$–C$_6$ alkynyl, C$_3$–C$_7$ cycloalkyl, C$_3$–C$_7$ cycloalkenyl, phenyl, benzyl, R$^8$ or R$^9$, said C$_1$–C$_6$ alkyl, C$_3$–C$_7$ cycloalkyl, phenyl and benzyl being optionally substituted by halo, —OR$^5$, —OR$^{10}$, —CN, —CO$_2$R$^7$, —OCONR$^5$R$^5$, —CONR$^5$R$^5$, —C(=NR$^5$)NR $^5$OR$^5$, —CONR$^5$NR$^5$R$^5$, —NR$^6$R$^6$, —NR$^5$R$^{10}$, —NR$^5$COR$^5$, —NR$^5$COR$^8$, —NR$^5$COR$^{10}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

R$^3$ is H, C$_1$–C$_6$ alkyl, C$_3$–C$_7$ cycloalkyl, phenyl, benzyl, halo, —CN, —OR$^7$, —CO$_2$R$^5$, —CONR$^5$R$^5$, R$^8$ or R$^9$, said C$_1$–C$_6$ alkyl, C$_3$–C$_7$ cycloalkyl, phenyl and benzyl being optionally substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$_5$CONR$^5$R$^5$, —NR$^5$SO$_2$R$^5$, R$^8$ or R$^9$;

R$^4$ is phenyl or naphthyl, each being optionally substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{11}$, So$_x$R$^6$, O—(C$_1$–C$_6$ alkylene)—CONR$^5$R$^5$, O—(C$_1$–C$_6$ alkylene)—NR$^5$R$^5$, or O_(C$_1$-C$_6$ alkylene) —OR$^6$;

each R$^5$ is independently either H, C$_1$–C$_6$ alkyl or C$_3$–C$_7$ cycloalkyl or, when two R$^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by $C_1$–$C_6$ alkyl or $C_3$–$C_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)—NR$^5$R$^5$, C$_1$–C$_6$ alkyl, fluoro(C$_1$–C$_6$)alkyl or C$_3$–C$_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C$_1$–C$_6$ alkyl, C$_3$–C$_7$ cycloalkyl, —SO$_2$R$^5$, —CONR$^5$R$^5$, —COOR$^5$, —CO—(C$_1$–C$_6$ alkylene)—OR$^5$ or —COR$^5$ and optionally substituted on a carbon atom which is not adjacent to a heteroatom by halo, —OR$^5$, —NR$^5$R$^5$, —NR$^5$COR$^5$, —NR$^5$COOR$^5$, —NR$^5$CONR$^5$R$^5$, —NR$^5$SO$_2$R$^5$ or —CN;

$R^{10}$ is $C_1$–$C_6$ alkyl substituted by $R^8$, $R^9$, —CONR$^5$R$^5$, —NR$^5$COR$^5$ or —NR$^5$R$^5$;

$R^{11}$ is phenyl optionally substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)—NR$^5$R$^5$, $C_1$–$C_6$ alkyl, halo(C$_1$–C$_6$)alkyl or $C_3$–$C_7$ cycloalkyl; and x and n are independently 0, 1 or 2.

2. A pharmaceutical composition comprising a compound according to claim 1 and one or more pharmaceutically acceptable excipients, diluents or carriers.

3. A pharmaceutical composition according to claim 2 comprising one or more additional therapeutic agents.

* * * * *

UNITED STATES PATENT AND TRADEMARK OFFICE
CERTIFICATE OF CORRECTION

| | | |
|---|---|---|
| PATENT NO. | : 7,157,468 B2 | Page 1 of 1 |
| APPLICATION NO. | : 10/669794 | |
| DATED | : January 2, 2007 | |
| INVENTOR(S) | : L. Jones et al. | |

It is certified that error appears in the above-identified patent and that said Letters Patent is hereby corrected as shown below:

Last Page, Column 38, Line 7    Insert: -OR$^5$,

INCORRECT:

$R^{10}$ is $C_1$-$C_6$ alkyl substituted by $R^8$, $R^9$, -CONR$^5$R$^5$, -NR$^5$COR$^5$ or -NR$^5$R$^5$;

CORRECT:

$R^{10}$ is $C_1$-$C_6$ alkyl substituted by $R^8$, $R^9$, -OR$^5$, -CONR$^5$R$^5$, -NR$^5$COR$^5$ or -NR$^5$R$^5$;

Signed and Sealed this

Tenth Day of April, 2007

JON W. DUDAS
*Director of the United States Patent and Trademark Office*